United States Patent
Tajong et al.

(10) Patent No.: US 12,427,218 B2
(45) Date of Patent: Sep. 30, 2025

(54) PORTABLE SANITIZING CLEANING DEVICE AND METHOD OF USE

(71) Applicant: 3 CAM G, LLC, Spring, TX (US)

(72) Inventors: Nelson Tajong, Spring, TX (US); Ndeloke Tajong, Spring, TX (US)

(73) Assignee: 3 CAM G, LLC, Spring, TX (US)

( * ) Notice: Subject to any disclaimer, the term of this patent is extended or adjusted under 35 U.S.C. 154(b) by 398 days.

(21) Appl. No.: 18/180,336

(22) Filed: Mar. 8, 2023

(65) Prior Publication Data

US 2023/0248872 A1 Aug. 10, 2023

Related U.S. Application Data

(63) Continuation-in-part of application No. 16/705,454, filed on Dec. 6, 2019, now abandoned.

(51) Int. Cl.
| | |
|---|---|
| *A47K 11/10* | (2006.01) |
| *A61L 2/18* | (2006.01) |
| *A61L 2/26* | (2006.01) |

(52) U.S. Cl.
CPC ...... *A61L 2/26* (2013.01); *A61L 2/18* (2013.01); *A61L 2202/15* (2013.01); *A61L 2202/16* (2013.01); *A61L 2202/181* (2013.01)

(58) Field of Classification Search
CPC .......... A47K 11/10; A47K 17/00; A47K 1/15; A47K 2/26; A47K 2/218; A47K 2202/15; A47K 2202/16; A47K 2202/181

USPC .......................................... 15/104.93, 104.94
See application file for complete search history.

(56) References Cited

U.S. PATENT DOCUMENTS

| | | | |
|---|---|---|---|
| 2005/0177964 A1* | 8/2005 | Cisneros ................ | A47K 11/10 15/210.1 |
| 2013/0152319 A1* | 6/2013 | Morrison, Jr. ......... | A47K 11/10 15/210.1 |
| 2014/0255269 A1* | 9/2014 | Kelly ....................... | A61L 2/18 422/292 |

* cited by examiner

*Primary Examiner* — Tom Rodgers

(57) ABSTRACT

An apparatus and method for use to allow for portably cleaning and sanitizing a surface, such as a toilet seat, using a flushable product. The surface cleaning device includes a body, and a front head comprising a wrapper encapsulating a wipe. The front head is then inserted into the body and the wrapper is rippable or tearable whereby a user may use a shearing motion to open the wrapper and expose a chemically impregnated wipe for sanitizing a surface. The surface cleaning device is designed to be lightweight, concealable, and portable such as to allow ease of use when carrying in a pocket, purse, or bag. Alternatively, the surface cleaning device may be provided in a dispensing device in or near a restroom, similar to dispensing devices that may hold sanitary napkins, tampons, or toilet seat covers.

4 Claims, 4 Drawing Sheets

PORTABLE SANITIZING CLEANING DEVICE AND METHOD OF USE

CROSS-REFERENCE TO RELATED APPLICATIONS

This application claims priority to U.S. non-provisional patent application Ser. No. 16/705,454, filed Dec. 6, 2019, which is incorporated by reference herein in its entirety.

STATEMENT REGARDING FEDERALLY SPONSORED RESEARCH

Not applicable.

BACKGROUND

The present invention generally relates to an improved portable, flushable, and biodegradable toilet seat disinfectant/cleaner.

There is a need for a portable and disposable public toilet seat disinfectant/cleaner. It is always a huge challenge for people with, or without, children and even adults when traveling or needing to use a public bathroom, to find a hygienic facility. Using a public bathroom is a challenge sometimes because people urinate on the toilet seat, and the next person to use the facility has to use toilet paper to clean someone else's urine, or even worse materials, before they can use the toilet.

The present invention is distinguished from the following applications and patents.

The present invention is distinguished from US 2004/0244130A1. The device of '130 is a toilet bowl cleaner that has a disposable cleaning head attached to a reusable handle and is intended for toilet bowl cleaning. The present invention is a toilet seat cleaner for personal use in public toilets and is one time use only, fully portable to be carried in pocket/purse/bag and is disposable, flushable, and biodegradable. In several embodiments, portions of the present invention are impregnated with non-abrasive or non-caustic chemicals and are impregnated with antibacterial and antiseptic chemicals.

The present invention is distinguished from US 2005/0166941 A1. The device of '941 is a toilet bowl cleaner with a plastic wand and a disposable brush head with a sponge applicator. The present invention is a toilet seat cleaner for personal use in public toilets and is one time use only, fully portable to be carried in pocket/purse/bag and is disposable, flushable, and biodegradable. In several embodiments, the present invention does not use a plastic wand, and in several embodiments, the present invention uses premoistened wipes mounted to a stick that are flushable/disposable, and biodegradable. In several embodiments, portions of the present invention are impregnated with non-abrasive or non-caustic chemicals and are impregnated with antibacterial and antiseptic chemicals.

The present invention is distinguished from US 2006/0225237A1. The device of '237 uses a reusable handle with a flushable head brush cleaner. The present invention is not reusable. In several embodiments, portions of the present invention are impregnated with non-abrasive or non-caustic chemicals and are impregnated with antibacterial and antiseptic chemicals.

The present invention is distinguished from U.S. Pat. No. 7,603,739. The device of '739 uses a reusable wand with a disposable attachment and is for toilet bowl. The present invention is not reusable. In several embodiments, the present invention uses premoistened wipes mounted to a stick that are flushable/disposable, and biodegradable. In several embodiments, portions of the present invention are impregnated with non-abrasive or non-caustic chemicals and are impregnated with antibacterial and antiseptic chemicals.

The present invention is distinguished from U.S. Pat. No. 7,827,648. The device of '648 is a brush head held in a cleaning device to clean toilet bowls. In several embodiments, the present invention has no reusable parts and does not use a brush, intended for one-time personal use only. In several embodiments, portions of the present invention are impregnated with non-abrasive or non-caustic chemicals and are impregnated with antibacterial and antiseptic chemicals.

The present invention is distinguished from U.S. Pat. No. 7,065,825. The device of '825 is a cleaning tool with a disposable scrubbing head. In several embodiments, the present invention is entirely disposable, flushable, and biodegradable, and it is for one time use only. In several embodiments, portions of the present invention are impregnated with non-abrasive or non-caustic chemicals and are impregnated with antibacterial and antiseptic chemicals.

The present invention is distinguished from CN101518427. The device of '427 is not meant to be for traveling, is for cleaning a toilet bowl, and has a reusable body. In several embodiments, portions of the present invention are impregnated with non-abrasive or non-caustic chemicals and are impregnated with antibacterial and antiseptic chemicals.

The present invention is distinguished from EP1553864. The product of '864 is a cleaning disposable brush head for toilet bowls that is replaceable. The product of '864 is not meant for travel. In several embodiments, portions of the present invention are impregnated with non-abrasive or non-caustic chemicals and are impregnated with antibacterial and antiseptic chemicals.

The present invention is distinguished from EP1736086. The product of '086 is a cleaning brush with a disposable head. In several embodiments, the present invention has all parts that will be disposable. In several embodiments, portions of the present invention are impregnated with non-abrasive or non-caustic chemicals and are impregnated with antibacterial and antiseptic chemicals.

The present invention is distinguished from U.S. Pat. No. 2,572,178. This product of '178 is meant for cleaning the entire toilet bowl. The handle or wand is extremely long as well, which fits the purpose for what it was created for, cleaning the toilet bowl. The wand is reusable. The device of '178 is not for travel purposes, and cannot be used in a dispenser for the entire cleaner. This device does not include a disinfectant. In several embodiments, portions of the present invention are impregnated with non-abrasive or non-caustic chemicals and are impregnated with antibacterial and antiseptic chemicals.

The present invention is distinguished from U.S. Pat. No. 2,648,085. The product of '085 is a swab for toilet bowls, again not for travel or use in public bathrooms. This swab pad is the only water degradable component. The pad is made of substantial thickness for scrubbing. In several embodiments, portions of the present invention are impregnated with non-abrasive or non-caustic chemicals and are impregnated with antibacterial and antiseptic chemicals.

The present invention is distinguished from U.S. Pat. No. 4,493,124. The product of '124 is for cleaning a toilet bowl, not for travel, and not small enough to fit into a purse/clutch. The cleaning tool is also reusable. In several embodiments, portions of the present invention are impregnated with non-abrasive or non-caustic chemicals and are impregnated with antibacterial and antiseptic chemicals.

The present invention is distinguished from U.S. Pat. No. 4,852,201. The product of '201 is for cleaning toilet bowls. The product of '201 is not for travel and single use. The product of '201 is not preloaded with disinfectants. In several embodiments, portions of the present invention are impregnated with non-abrasive or non-caustic chemicals and are impregnated with antibacterial and antiseptic chemicals.

The present invention is distinguished from U.S. Pat. No. 5,630,243. The product of '243 is a toilet bowl cleaner with a disposable pad, is not meant for travel, and is not preloaded with disinfectants. In several embodiments, portions of the present invention are impregnated with non-abrasive or non-caustic chemicals and are impregnated with antibacterial and antiseptic chemicals.

The present invention is distinguished from U.S. Pat. No. 6,880,197. The product of '197 is not made to be flushed down the toilet. The entire unit is disposable in a trash can. The product is not meant for travel. The neck is flexible to be used to clean a toilet bowl. In several embodiments, portions of the present invention are impregnated with non-abrasive or non-caustic chemicals and are impregnated with antibacterial and antiseptic chemicals.

The present invention is distinguished from U.S. Pat. No. 7,127,768. The product of '768 is designed for cleaning an entire toilet bowl with a flexible reusable head. In several embodiments, portions of the present invention are impregnated with non-abrasive or non-caustic chemicals and are impregnated with antibacterial and antiseptic chemicals.

The present invention is distinguished from U.S. Pat. No. 7,159,265. The device of '265 is intended for use to clean the toilet bowl; it is a scrubbing brush with a replaceable head. The wand is made out of plastic. In several embodiments, portions of the present invention are impregnated with non-abrasive or non-caustic chemicals and are impregnated with antibacterial and antiseptic chemicals.

The present invention is distinguished from U.S. Pat. No. 7,287,295. The product of '295 is designed for cleaning the entire toilet unit, including the bowl. The handle is reusable and can be hung as a single unit. The device of '295 is not meant for traveling, and cannot be carried in a clutch/purse for traveling. In several embodiments, portions of the present invention are impregnated with non-abrasive or non-caustic chemicals and are impregnated with antibacterial and antiseptic chemicals.

The present invention is distinguished from U.S. Pat. No. 7,530,138. The product of '138 is a toilet bowl cleaning tool with a disposable swab. It is not meant for travel and cannot fit into a purse/clutch for travel and personal use in public toilets. It is not completely flushable, just the swab is flushable. In several embodiments, portions of the present invention are impregnated with non-abrasive or non-caustic chemicals and are impregnated with antibacterial and antiseptic chemicals.

The present invention is distinguished from US 2002/0054784. The invention of '784 is a cleaning brush. The detergent is contained in the handle of the brush, and also it is not meant for personal travel and cannot fit into a clutch/purse. In several embodiments, portions of the present invention are impregnated with non-abrasive or non-caustic chemicals and are impregnated with antibacterial and antiseptic chemicals.

The present invention is distinguished from US 2004/0019996. The invention of '996 is a toilet brush made of plastic or foam. This product cannot be flushed down the toilet, it is only disposed in an environmentally sound manner. This does not have a disinfectant attached to the cleaning sponge. This toilet brush is not meant to be portable for personal travel, and cannot fit into a clutch/purse. The sponge portion is not detachable and cannot be flushed. In several embodiments, portions of the present invention are impregnated with non-abrasive or non-caustic chemicals and are impregnated with antibacterial and antiseptic chemicals.

The present invention is distinguished from US2009/0163126. The product of '126 is intended for cleaning toilet bowls. The product has two surfaces for cleaning, and it has a multi-use head. None of the parts of the brush are flushable. The head and wand are reusable. This is not for personal travel and cannot fit into a clutch/purse. In several embodiments, portions of the present invention are impregnated with non-abrasive or non-caustic chemicals and are impregnated with antibacterial and antiseptic chemicals.

SUMMARY

In some embodiments of the present invention, the present invention is a system and method for use of portably cleaning and sanitizing a surface, such as a toilet seat, using a flushable product.

One embodiment of the present invention is a disposable/flushable product that an individual can buy and carry with them when they travel, or need to use a public bathroom, to disinfect the toilet seat before sitting on it.

In several embodiments, the present invention can have a wand that prevents an individual from actually touching the toilet seat with their hands while cleaning it.

In several embodiments, the invention is meant to be lightweight, portable, travel size, disposable, biodegradable, flushable, for single use, and can fit in a woman's clutch or purse just like a tampon.

In several embodiments, the invention is designed such that public bathrooms can provide the invention in a dispenser for people to use to disinfect the toilet seat before use just like they provide the paper toilet seat cleaner.

In several embodiments, the present invention will be designed for cleaning the toilet seat and disinfecting the toilet seat before personal use.

In several embodiments, the present invention is not intended to be a toilet brush but is designed to clean any dirt/body fluids on the toilet seat before use.

Some of the products have a reusable part. Present invention does not have a reusable part; it will be completely disposable and flushable.

Some of the products have a flushable head, but the wand is reusable; with present invention the wand will not be reusable. It is meant for a one-time use.

Some of these products are meant to be used for cleaning bathrooms at home, but the goal of the present invention is for people to be able to use the product to clean public bathrooms before using it.

None of these products for cleaning toilets are portable and intended for travel. The goal of the present invention is to make a product that is portable, and is small enough to fit into a clutch/purse so individuals can purchase it for travel or for use in public toilets, like parks and fairs, to disinfect the seat before use.

Public bathrooms do not have any toilet seat cleaner/disinfectant in the United States that people can use while in a public bathroom. A lot of bathrooms do provide a toilet seat paper cover, but there is a need for some kind of disinfectant or cleaner before placing the toilet seat paper covers that are currently being provided by most bathrooms. The goal of this product is to have a cleaner/disinfectant that can be put in wall-mounted dispensers in public toilets just like they put the paper seat covers that people can use to disinfect the seat before using the toilet.

In several embodiments, the present invention is an improved surface cleaning device comprising; a body; said body further comprising; being biodegradable, semi-rigid, and of semi-tubular geometry a front head attachment; said front head attachment further comprising; being biodegradable, and semi-rigid and a front head; said front head further comprising; being biodegradable, semi-rigid, and impregnated with one or more of the following: non-abrasive, non-caustic, antibacterial or antiseptic chemicals, wherein said front head attachment is mechanically attached to said body, and said front head attachment is mechanically attached to said front head.

In several embodiments, said body, said front head attachment, and said front head are comprised of one single unit. In several embodiments, said front head is fan shaped. In several embodiments, said front head is ball/wad shaped. In several embodiments, said front head is a sponge. In several embodiments, said front head is multiple strips. In several embodiments, said body, said front head attachment, and said front head are comprised of one single unit and are encapsulated in a wrapper unit. In several embodiments, said body is encapsulated in a back-housing unit. In several embodiments, said front head is encapsulated in a front housing unit. In several embodiments, said front head is detachable from said front head attachment.

BRIEF DESCRIPTION OF THE DRAWINGS

For a more complete understanding of the present disclosure and the advantages thereof, reference is now made to the following descriptions to be taken in conjunction with the accompanying drawings describing specific embodiments of the disclosure, wherein.

DETAILED DESCRIPTION

Figure 1:
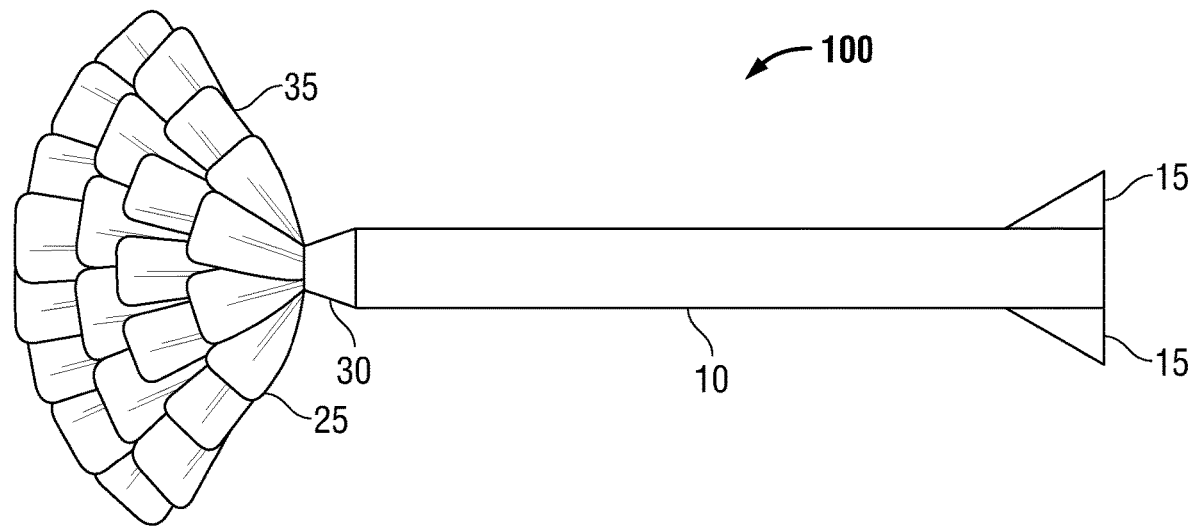
FIG. 1 illustrates one embodiment of the present invention in a side view.

One or more illustrative embodiments incorporating the invention disclosed herein are presented below. Applicant has created a revolutionary system and method for use of portably cleaning and sanitizing a surface, such as a toilet seat, using a flushable product.

In the following description, certain details are set forth such as specific quantities, sizes, etc. to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing embodiments of the disclosure and are not intended to be limiting thereto. Drawings are not necessarily to scale and arrangements of specific units in the drawings can vary.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless, or essentially meaningless, the definition should be taken from Webster's Dictionary 2022. Definitions and/or interpretations should not be incorporated from other patent applications, patents, or publications, related or not, unless specifically stated in this specification, or if the incorporation is necessary for maintaining validity. As utilized herein, the following terms have the following definitions.

As defined herein, "non-abrasive" and/or "non-caustic chemicals" will include, but are not limited to, hydrogen peroxide, isopropyl alcohol, and/or ethanol in conjunction with a detergent or alone. All chemicals will be environmentally safe and nontoxic to skin.

As defined herein, "antibacterial and/or antiseptic chemicals" will include, but are not limited to, hydrogen peroxide, isopropyl alcohol, and/or ethanol in conjunction with a detergent or alone. All chemicals will be environmentally safe and nontoxic to skin.

Certain terms are used in the following description and claims to refer to system components. As one skilled in the art will appreciate, different persons may refer to a component by different names. This document does not intend to distinguish between components that differ in name, but not function. The drawing figures are not necessarily to scale. Certain features of the invention may be shown exaggerated in scale or in somewhat schematic form, and some details of conventional elements may not be shown, all in the interest of clarity and conciseness.

Although several preferred embodiments of the present invention have been described in detail herein, the invention is not limited hereto. It will be appreciated by those having ordinary skill in the art that various modifications can be made without materially departing from the novel and advantageous teachings of the invention. Accordingly, the embodiments disclosed herein are by way of example. It is to be understood that the scope of the invention is not to be limited thereby.

In general, the apparatus, systems and methods of the present disclosure are distinguished from and advantageous over other systems and methods for use of portably cleaning and sanitizing a surface such as a toilet seat using a flushable product.

FIG. 1 illustrates one embodiment of the present invention in a side view. As illustrated, in several embodiments, surface cleaning device 100 can be comprised of one solid piece of material.

In several embodiments, surface cleaning device 100 is designed to be biodegradable. In several embodiments, surface cleaning device 100 is designed to be flushable down a toilet. In several embodiments, surface cleaning device 100 is designed to be comprised of a solid semirigid paper material. In several embodiments, surface cleaning device 100 is designed to have one use before being disposed. In several embodiments, surface cleaning device 100 is designed to be portable. In several embodiments; surface cleaning device 100 is designed to be impregnated with non-abrasive or non-caustic chemicals. In several embodiments, surface cleaning device 100 is designed to be impregnated with antibacterial and antiseptic chemicals.

In several embodiments, surface cleaning device 100 is designed have a body 10 and holding grips 15. In several embodiments, body 10 can be comprised of one solid piece of material. In several embodiments, body 10 is designed to be biodegradable. In several embodiments, body 10 is designed to be flushable down a toilet. In several embodiments, body 10 is designed to be comprised of a solid semirigid paper material. In several embodiments, body 10 is designed to have one use before being disposed. In several embodiments, body 10 is designed to be semi-tubular in shape. In several embodiments, body 10 is hollow.

In several embodiments, body 10 has a front head attachment 30. In several embodiments, front head attachment 30 can be comprised of one solid piece of material. In several embodiments, front head attachment 30 is designed to be biodegradable. In several embodiments, front head attachment 30 is designed to be flushable down a toilet. In several embodiments, front head attachment 30 designed to be comprised of a solid semirigid paper material. In several embodiments, front head attachment 30 is designed to have one use before being disposed. In several embodiments, front head attachment 30 is designed to be conical in shape, although other geometric shapes can be used. In several embodiments, front head attachment 30 is hollow. In several embodiments, front head attachment 30 attaches front head 25 to body 10.

In several embodiments, front head 25 can be comprised of one solid piece of material. In several embodiments, front head 25 can be comprised of several pieces of material. In several embodiments, front head 25 is designed to be biodegradable. In several embodiments, front head 25 is designed to be flushable down a toilet. In several embodiments, front head 25 is designed to be comprised of a solid semirigid paper material. In several embodiments, front head 25 is designed to have one use before being disposed. In several embodiments, front head 25 is designed to be fan-shaped, although other geometric shapes can be used. In several embodiments, front head 25 is designed to be impregnated with non-abrasive or non-caustic chemicals. In several embodiments, front head 25 is designed to be impregnated with antibacterial and antiseptic chemicals. In several embodiments, front head 25 is comprised of several fronds, or feathers 35 which attach to the front head attachment 30.

In several embodiments, the surface cleaning device 100 can be used to clean and disinfect surfaces, such as but not limited to, toilet seats, car seats, counters, shopping carts, handrails, door handles, or other surfaces that may need cleaning and disinfecting prior to use.

Figure 2:
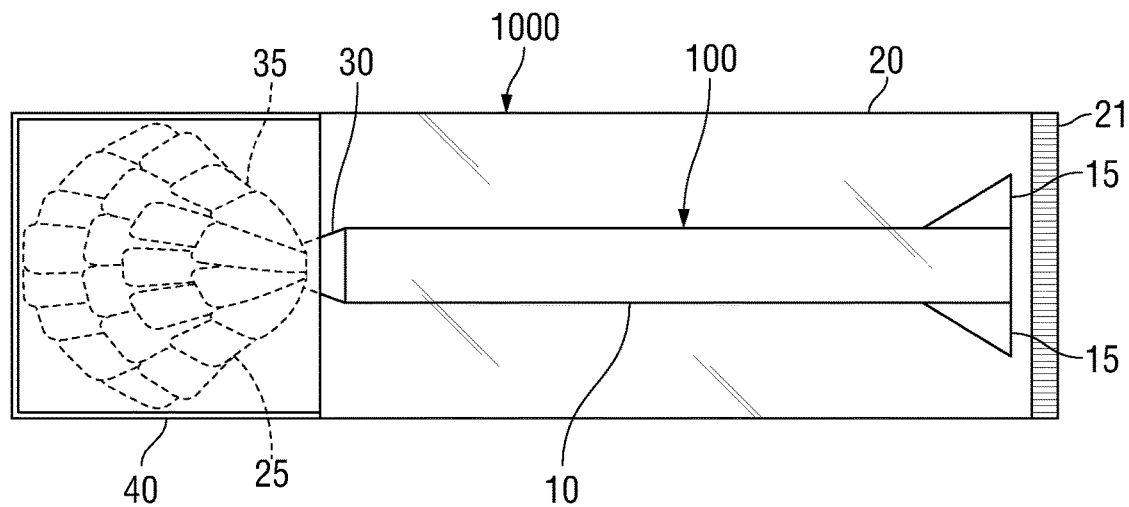
FIG. 2 illustrates one embodiment of the present invention in a side view in a wrapper.

FIG. 2 illustrates one embodiment of the present invention in a side view in a wrapper. As shown, components of FIG. 1 are shown in a complete wrapped unit 1000. As illustrated, in some embodiments, wrapped unit 1000 has two housing units 40 and 20. Front housing unit 40 is designed to separate the chemically impregnated front head 25 from the body 10 which is housed in the back unit 20. Back unit 20 is preferably a dry housing. Both back unit 20 and front unit 40 can be opened by ripping seal 21.

Figure 3:
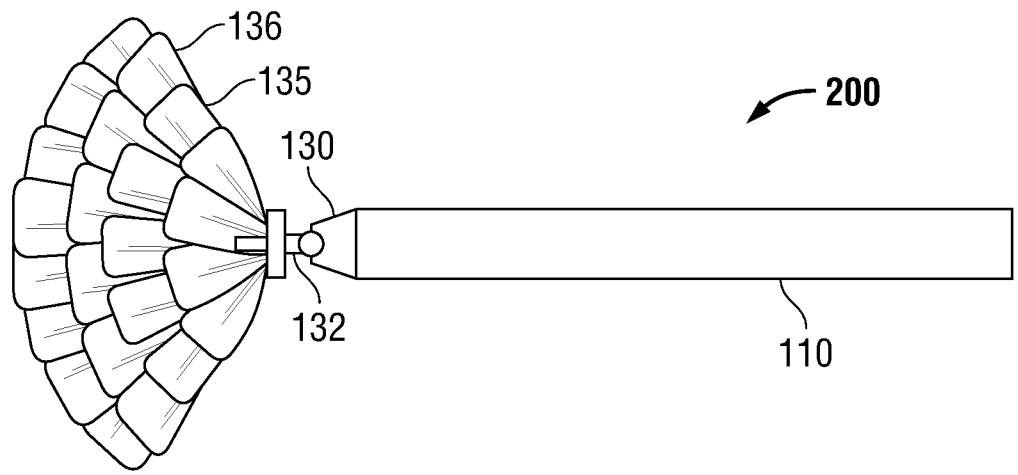
FIG. 3 illustrates one embodiment of the present invention in a side view with attached front head.

FIG. 3 illustrates one embodiment of the present invention in a side view with attached front head 135. As illustrated, in several embodiments, surface cleaning device 200 can be comprised of two solid pieces of material. In several embodiments, surface cleaning device 200 is designed to be biodegradable. In several embodiments, surface cleaning device 200 is designed to be flushable down a toilet. In several embodiments, surface cleaning device 200 is designed to be comprised of a solid semirigid paper material. In several embodiments, surface cleaning device 200 is designed to have one use before being disposed. In several embodiments, surface cleaning device 200 is designed to be portable. In several embodiments, surface cleaning device 200 is designed to be impregnated with non-abrasive or non-caustic chemicals. In several embodiments, surface cleaning device 200 is designed to be impregnated with antibacterial and antiseptic chemicals.

In several embodiments, surface cleaning device 200 is designed have a body 110. In several embodiments, body 110 can be comprised of one solid piece of material. In several embodiments, body 110 is designed to be biodegradable. In several embodiments, body 110 is designed to be flushable down a toilet. In several embodiments, body 110 is designed to be comprised of a solid semirigid paper material. In several embodiments, body 110 is designed to have one use before being disposed. In several embodiments, body 110 is designed to be semi tubular in shape. In several embodiments, body 110 is hollow.

In several embodiments, body 110 has a front head attachment 130. In several embodiments, front head attachment 130 can be comprised of one solid piece of material. In several embodiments, front head attachment 130 is designed to be biodegradable. In several embodiments, front head attachment 130 is designed to be flushable down a toilet. In several embodiments, front head attachment 130 is designed to be comprised of a solid semirigid paper material. In several embodiments, front head attachment 130 is designed to have one use before being disposed. In several embodiments, front head attachment 130 is designed to be conical in shape, although other geometric shapes can be used. In several embodiments, front head attachment 130 is hollow. In several embodiments, front head attachment 130 attaches front head 135 to body 110 via attachment interface 132. In several embodiments, front head 135 can be comprised of one solid piece of material.

In several embodiments, front head 135 can be comprised of several pieces of material. In several embodiments, front head 135 is designed to be biodegradable. In several embodiments, front head 135 is designed to be flushable down a toilet. In several embodiments, front bead 135 is designed to be comprised of a solid semirigid paper material. In several embodiments, front head 135 is designed to have one use before being disposed. In several embodiments, front head 135 is designed to be fan-shaped, although other geometric shapes can be used. In several embodiments, front head 135 is designed to be impregnated with non-abrasive or non-caustic chemicals. In several embodiments, front head 135 is designed to be impregnated with antibacterial and antiseptic chemicals. In several embodiments, front head 135 is comprised of several fronds, or feathers 136 which attach to the front head attachment 130 via attachment interface 132. In several embodiments of the present invention, attachment interface 132 can pivot about front head attachment 130.

Figure 4:
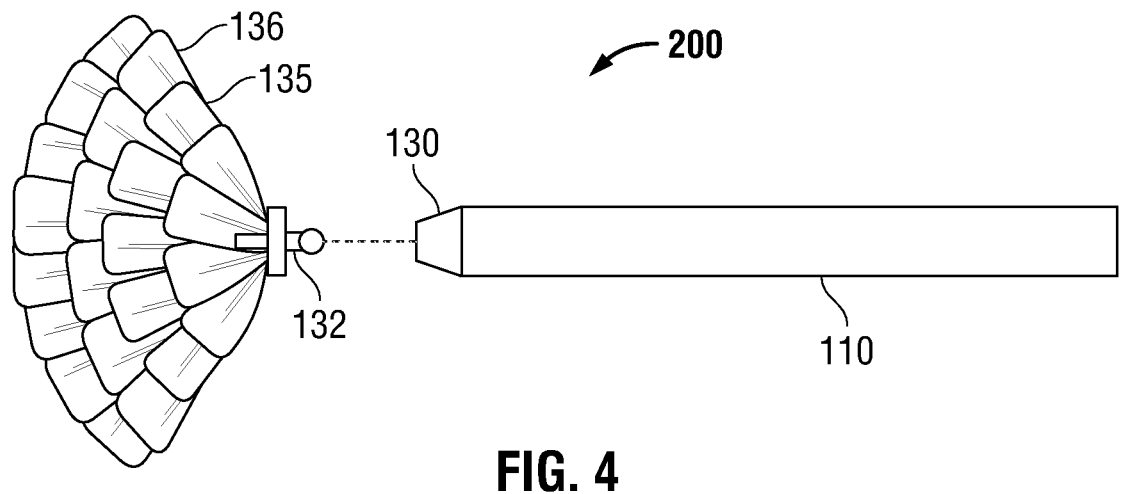
FIG. 4 illustrates one embodiment of the present invention in a side view with the front head detached.

FIG. 4 illustrates one embodiment of the present invention in a side view with attached front head 135 detached from front head attachment 130.

Figure 5:
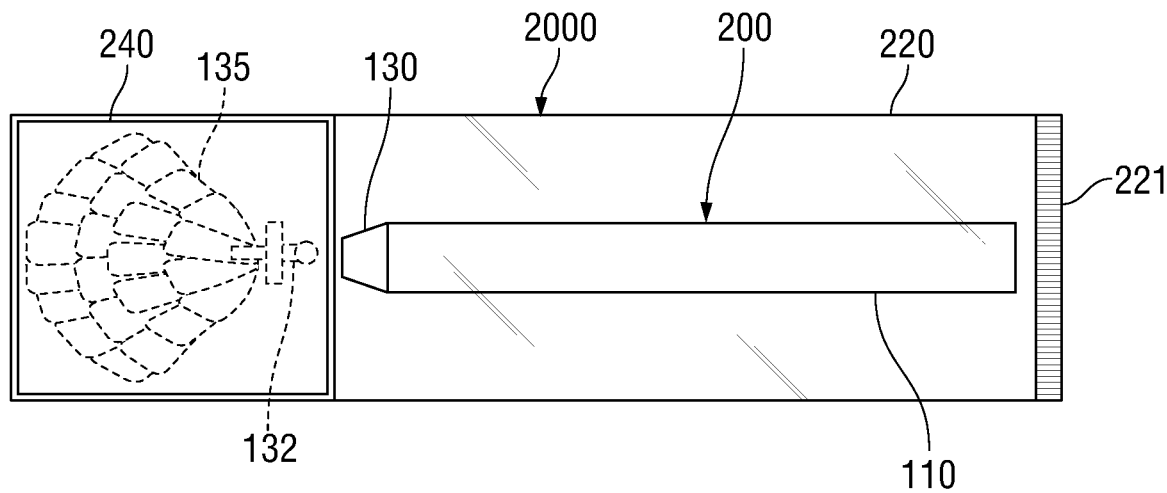
FIG. 5 illustrates one embodiment of the present invention in a side view with the front head detached in a wrapper.

FIG. 5 illustrates one embodiment of the present invention in a side view with the front head 135 detached in a wrapper. As shown, components of FIG. 5 are shown in a complete wrapped unit 2000. As illustrated, in some embodiments, wrapped unit 2000 has two housing units 240 and 220. Front housing unit 240 is designed to separate the chemically impregnated front head 135 from the body 110 which is housed in the back unit 220. Back unit 220 is preferably a dry housing. Both back unit 220 and front unit 240 can be opened by ripping seal 221.

Figure 6:
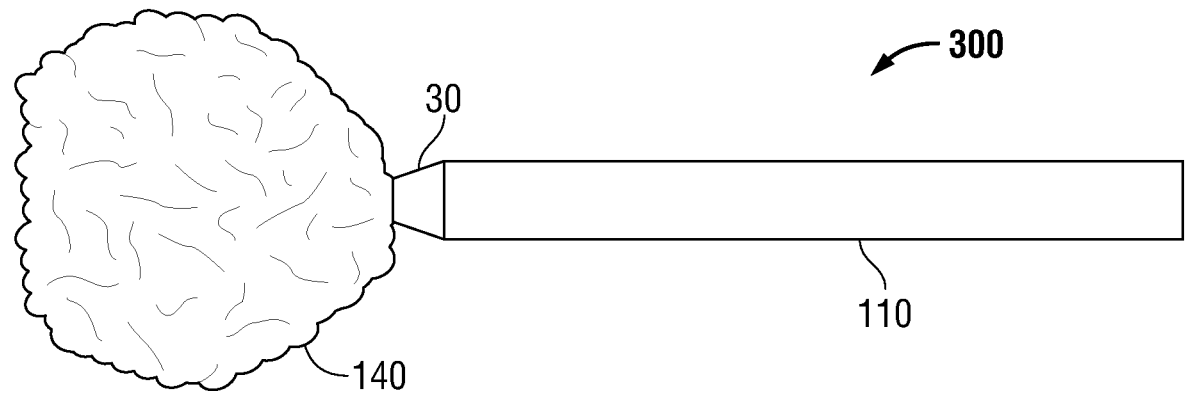
FIG. 6 illustrates one embodiment of the present invention in a side view with an alternate front head.

FIG. 6 illustrates one embodiment of the present invention in a side view with an alternate front head 140. In several embodiments, surface cleaning device 300 is designed have a body 110. In several embodiments, body 110 can be comprised of one solid piece of material. In several embodiments, body 110 is designed to be biodegradable. In several embodiments, body 110 is designed to be flushable down a toilet. In several embodiments, body 110 is designed to be comprised of a solid semirigid paper material. In several embodiments, body 110 is designed to have one use before being disposed. In several embodiments, body 110 is designed to be semi tubular in shape. In several embodiments, body 110 is hollow.

In several embodiments, alternate front head 140 can be comprised of one solid piece of material. In several embodiments, alternate front head 140 can be comprised of a sponge type of material. In several embodiments, alternate front head 140 is designed to be biodegradable. In several embodiments, alternate front head 140 is designed to be flushable down a toilet. In several embodiments, alternate front head 140 is designed to be comprised of a solid semirigid paper material. In several embodiments, alternate front head 140 is designed to have one use before being disposed. In several embodiments, alternate front head 140 is impregnated with to be impregnated with non-abrasive or non-caustic chemicals. In several embodiments, alternate front head 140 is designed to be impregnated with antibacterial and antiseptic chemicals. In several embodiments, alternate front head 140 attaches to the front head attachment 30.

Figure 7:
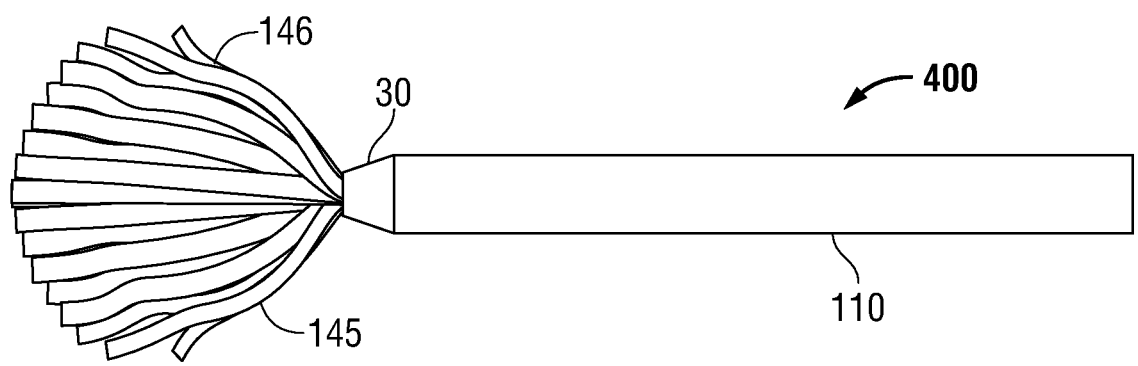
FIG. 7 illustrates one embodiment of the present invention in a side view with an alternate front head.

FIG. 7 illustrates one embodiment of the present invention in a side view with an alternate front head 145. In several embodiments, surface cleaning device 400 is designed have a body 110. In several embodiments, body 110 can be comprised of one solid piece of material. In several embodiments, body 110 is designed to be biodegradable. In several embodiments, body 110 is designed to be flushable down a toilet. In several embodiments, body 110 is designed to be comprised of a solid semirigid paper material. In several embodiments, body 110 is designed to have one use before being disposed. In several embodiments, body 110 is designed to be semi-tubular in shape. In several embodiments, body 110 is hollow.

In several embodiments, alternate front head 145 can be comprised of multiple strips 146 of material. In several embodiments, alternate front head 145 is designed to be biodegradable. In several embodiments, alternate front head 145 is designed to be flushable down a toilet. In several embodiments, alternate front head 145 and multiple strips 146 are designed to be comprised of a solid semirigid paper material. In several embodiments, alternate front head 145 is designed to have one use before being disposed. In several embodiments, alternate front head 145 is designed to be impregnated with non-abrasive or non-caustic chemicals. In several embodiments, alternate front head 145 is designed to be impregnated with antibacterial and antiseptic chemicals. In several embodiments, alternate front head 145 attaches to the front head attachment 30.

Figure 8:
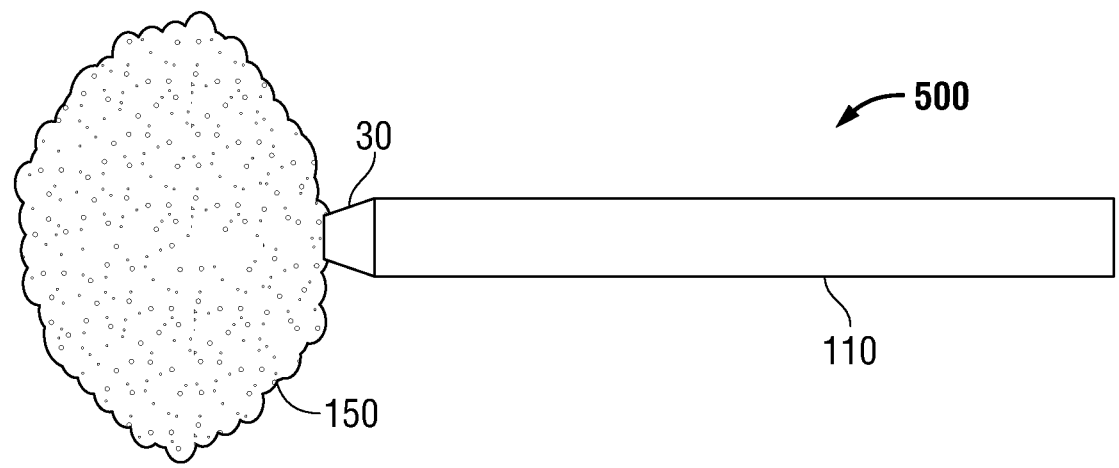
FIG. 8 illustrates one embodiment of the present invention in a side view with an alternate front head.

FIG. 8 illustrates one embodiment of the present invention in a side view with an alternate front head 150. In several embodiments, surface cleaning device 500 is designed have a body 110. In several embodiments, body 110 can be comprised of one solid piece of material. In several embodiments, body 110 is designed to be biodegradable. In several embodiments, body 110 is designed to be flushable down a toilet. In several embodiments, body 110 is designed to be comprised of a solid semirigid paper material. In several embodiments, body 110 is designed to have one use before being disposed. In several embodiments, body 110 is designed to be semi-tubular in shape. In several embodiments, body 110 is hollow.

In several embodiments, alternate front head 150 can be comprised of one solid piece of material. In several embodiments, alternate front head 150 can be comprised of a ball/wad type of material. In several embodiments, alternate front head 150 is designed to be biodegradable. In several embodiments, alternate front head 150 is designed to be flushable down a toilet. In several embodiments, alternate front head 150 is designed to be comprised of a solid semirigid paper material. In several embodiments, alternate front head 150 is designed to have one use before being disposed. In several embodiments, alternate front head 150 is designed to be impregnated with non-abrasive or non-caustic chemicals. In several embodiments, alternate front head 150 is designed to be impregnated with antibacterial and antiseptic chemicals. In several embodiments, alternate front head 150 attaches to the front head attachment 30.

In several embodiments, a user can take one of the surface cleaning devices 100, 200, 300, 400, 500, or 600, which has front head 25, 135, 140, 145, 150, or 610 which is impregnated with antibacterial and antiseptic chemicals, and can swipe the surface which is desired to be cleaned with front head 25, 135, 140, 145, 150, or 610. After cleaning the surface, surface cleaning device 100, 200, 300, 400, 500, or 600 can be thrown away in a trash receptacle, or thrown into a toilet bowl to be flushed, as surface cleaning device 100, 200, 300, 400, 500, or 600 is, in many embodiments, biodegradable and/or water soluble. In several embodiments, surface cleaning device 100, 200, 300, 400, 500, or 600 is compact, and can fit in a person's pocket, purse, bag, or clutch. In several embodiments, wrapper 1000, 2000, or 620 is moisture proof.

Figure 9:
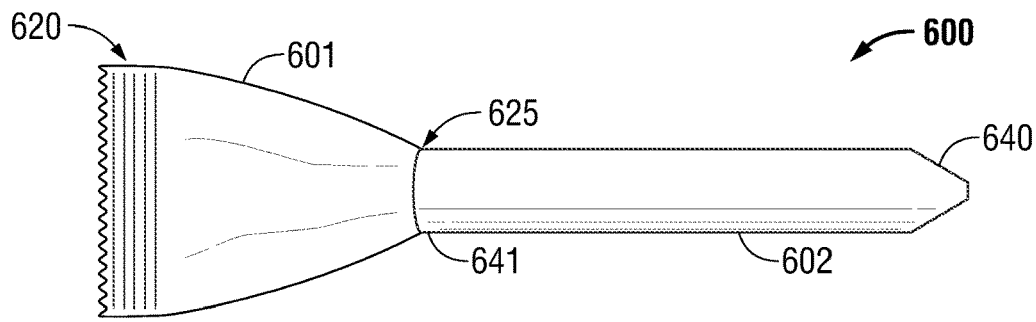
FIG. 9 illustrates an embodiment of the present invention in a side view.

FIG. 9 illustrates an embodiment of the invention in a side view. In several embodiments, surface cleaning device 600 is designed to have a body 602. In several embodiments, body 602 can be comprised of one solid piece of material. In several embodiments, body 502 is designed to be biodegradable. In several embodiments, body 602 is designed to be flushable down a toilet. In several embodiments, body 602 is designed to be comprised of a solid semirigid paper material. In several embodiments, body 602 is designed to have one use before being disposed. In several embodiments, body 602 is designed to be semi-tubular in shape. In several embodiments, body 602 is hollow.

In several embodiments, the surface cleaning device 600 is comprised of body 602 having a substantially tubular geometry. The body 602 comprises a proximal end 641 proximate to front head 601 and a distal end 602 opposite the proximal end 641. In some embodiments, the body 602 is hollow. The body 602 further comprises a cavity 625 for receiving front head 601. Front head 601 is comprised of wrapper 620, wipe 610 (shown in FIG. 10), and may include an adhesive 603 (shown in FIG. 11). In alternative embodiments, adhesive 602 is not required as the front head 601 may simply be inserted into the cavity 625. In some embodiments, a portion of front head 601 may substantially extend through body 602 or even extend a substantial length of the body 602 to the distal end 640. In some embodiments, the wrapper 620 is rippable or tearable in that a person may grasp either corner of the wrapper and create a shearing motion to open the wrapper and expose the wipe 610 encapsulated within the wrapper 620. The wrapper 620, in some embodiments, is moisture proof to seal in the impregnated chemicals, as described herein, and to further prevent said chemicals from leeching into or wetting the body 602. Such leeching or wetting of the body 602 may cause pre-mature degradation of the body's structure being that the body 602 may be biodegradable and/or flushable in some embodiments.

In several embodiments, surface cleaning device 600 is designed to be biodegradable. In several embodiments, surface cleaning device 600 is designed to be flushable down a toilet. In several embodiments, surface cleaning device 600 is designed to be comprised of a solid semi-rigid paper material. In several embodiments, surface cleaning device 600 is designed to have one use before being disposed. In several embodiments, surface cleaning. device 600 is designed to be portable and lightweight, that is able to easily and discretely carried in a person's pocket, purse, or bag. In several embodiments; surface cleaning device 600 is designed to be impregnated with non-abrasive or non-caustic chemicals. In several embodiments, surface cleaning device 600 is designed to be impregnated with antibacterial and antiseptic chemicals, such as a 75% ethyl alcohol.

In several embodiments, wipe 610 may be comprised of one solid piece of material. In several embodiments, wipe 610 can be comprised of several pieces of material. In several embodiments, wipe 610 is designed to be biodegradable. In several embodiments, wipe 610 is designed to be flushable down a toilet. In several embodiments, wipe 610 is designed to have one use before being disposed. In several embodiments, wipe 610 is designed to be fan-shaped, although other geometric shapes can be used. In several embodiments, wipe 610 is designed to be impregnated with non-abrasive or non-caustic chemicals. In several embodiments, wipe 610 is designed to be impregnated with antibacterial and antiseptic chemicals.

In several embodiments, the surface cleaning device 600 can be used to clean and disinfect surfaces, such as but not limited to, toilet seats, car seats, counters, shopping carts, handrails, door handles, or other surfaces that may need cleaning and disinfecting prior to use.

Figure 10:
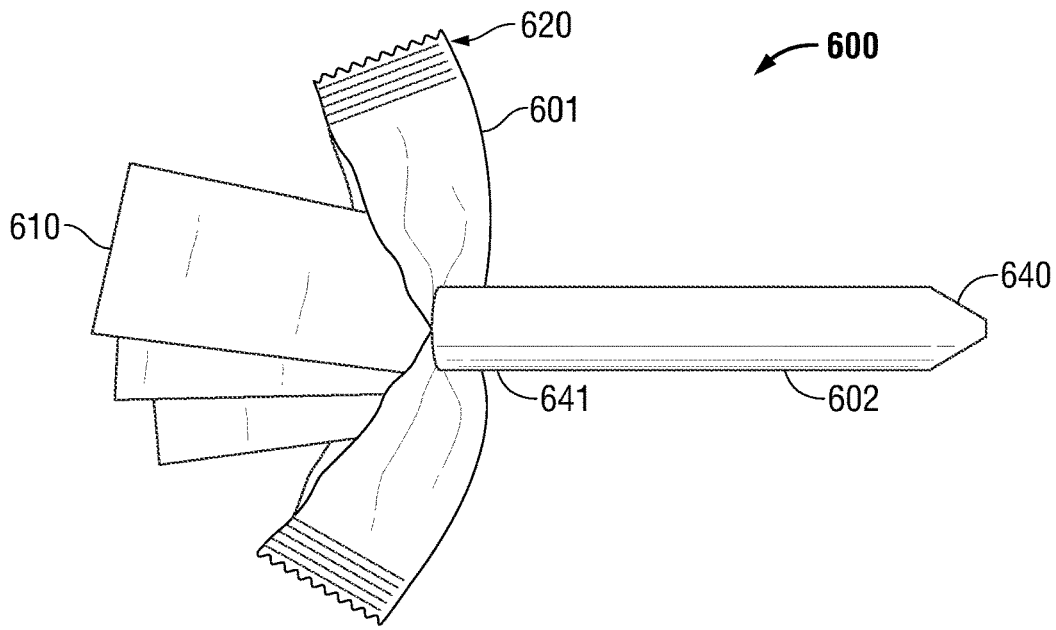
FIG. 10 illustrates the embodiment of FIG. 9 with the "open" side view.

FIG. 10 illustrates an embodiment of surface cleaning device 600 wherein a wrapper 620 of a front head 601 is in an open state exposing a wipe 610 impregnated with chemicals, as described herein. In some embodiments, the wrapper 620 is rippable or tearable in that a person may grasp either corner of the wrapper and create a shearing motion to open the wrapper and expose the wipe 610 encapsulated within the wrapper 620. The wrapper 620, in some embodiments, is moisture proof to seal in the impregnated chemicals, as described herein, and to further prevent said chemicals from leeching into or wetting the body 602. Such leeching or wetting of the body 602 may cause pre-mature degradation of the body's structure being that the body 602 may be biodegradable and/or flushable in some embodiments. The design of surface cleaning device 600 provides an easy to grip body 602 which allows a person to hold said body and use the exposed chemically impregnated wipe 610 to sanitize a toilet seat, or other items as described herein. The chemically impregnated wipe 610 may comprise a single wipe folded, rolled, or wadded into a shape or may comprise multiple strips of paper, cloth, or other material.

Figure 11:
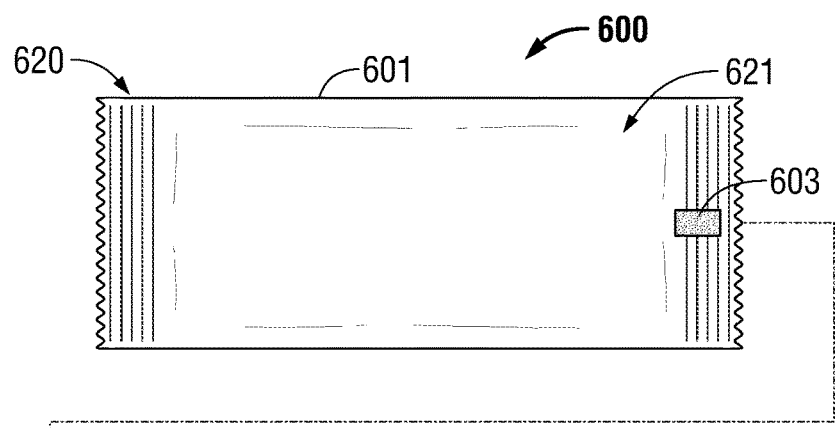
FIG. 11 illustrates the embodiment of FIG. 9 in an "exploded" view.

FIG. 11 illustrates an exploded view of an embodiment of the surface cleaning device 600. Of particular interest with this embodiment is the adhesive 603 applied to an outer surface 621 of the wrapper 620 of the front head 601. The portion of the wrapper 620 with the applied adhesive is inserted into cavity 625 of body 602. The wrapper 620 may be rolled, wadded, or stuffed into cavity 625. The use of adhesive or other means to attach the front head 601 and particularly wrapper 620 is to create bond between the wrapper 620 and an inner surface of body 602 which is achieved by insertion of the adhesive applied wrapper 620 into cavity 625. The adhesive 603 may be applied directly to a surface 621 of wrapper 620 or injected into the cavity 625 before or during insertion of wrapper 620 into said cavity. Adhesives may include glue, epoxy, or friction fit. Alternatively, wrapper 620 may be inserted into a substantial length of body 602 via cavity 625 and use friction to hold the wrapper 620 and front head 601 in place against an inner surface of body 602 within cavity 625. Embodiments of the surface cleaning device 600 that use an adhesive 603 provide better results than embodiments without an adhesive connection between the wrapper 620 and body 602. Use of an adhesive results in less chance or opportunity for the wrapper to accidentally be removed from the cavity 625 during normal or typical use.

While preferred embodiments have been shown, and described, modifications thereof can be made by one skilled in the art without departing from the scope or teaching herein. The embodiments described herein are exemplary only and are not limiting. Many variations and modifications of the system and apparatus are possible and will become apparent to those skilled in the art once the above disclosure is fully appreciated. For example, the relative dimensions of various parts, the materials from which the various parts are made, and other parameters can be varied.

What is claimed is the following:

1. A portable, one-time use sanitizing device for sanitizing a surface comprising:
　　a body, said body being semi-tubular, bio-degradable, flushable, and semi-rigid and further comprising a proximate end and a distal end, said proximate end of said body further comprises a cavity;
　　a front head, said front head comprising a wrapper having an exterior surface, wherein said wrapper encapsulates a wipe; wherein said wipe is biodegradable, flushable, and impregnated with a chemical, wherein said chemical is comprised of one or more of the following: a non-abrasive, non-caustic, antibacterial, or antiseptic chemical, further wherein, said wrapper is rippable and moisture proof; and wherein
　　said front head is partially inserted into said cavity formed at the proximate end of said body
　　an adhesive, wherein said adhesive is applied between said exterior surface of said wrapper and an inner surface of said cavity of said body.

2. The portable one-time use sanitizing device for sanitizing a surface of claim 1, wherein said adhesive is a glue.

3. The portable one-time use sanitizing device for sanitizing a surface of claim 1, wherein said adhesive is an epoxy.

4. The portable one-time use sanitizing device for sanitizing a surface of claim 1, wherein said front head extends into a length of said cavity and wherein said front head uses friction to hold said wrapper within said cavity.

* * * * *